United States Patent [19]

Rycroft

[11] Patent Number: 4,758,230

[45] Date of Patent: Jul. 19, 1988

[54] SYRINGE BARREL ASSEMBLY

[75] Inventor: Alan K. Rycroft, Rutherford, N.J.

[73] Assignee: Becton, Dickinson and Company, Franklin Lakes, N.J.

[21] Appl. No.: 831,736

[22] Filed: Feb. 20, 1986

[51] Int. Cl.$^4$ ............................................. A61M 5/00
[52] U.S. Cl. .................................. 604/118; 604/201;
604/206; 206/366
[58] Field of Search ............... 604/187, 192, 198, 201,
604/204, 206; 206/366, DIG. 820,

[56] References Cited

U.S. PATENT DOCUMENTS

| | | | |
|---|---|---|---|
| D. 282,348 | 1/1986 | Federighi | D9/341 |
| 2,616,420 | 11/1952 | Hart | 604/201 |
| 2,828,742 | 4/1958 | Ashkenaz | 604/206 |
| 2,880,723 | 4/1959 | Adams | 604/201 |
| 3,305,084 | 2/1967 | Higgins et al. | 206/366 |
| 3,917,120 | 11/1975 | Larenz et al. | 206/366 |
| 4,142,633 | 3/1979 | Raghavachari et al. | 206/366 |
| 4,148,316 | 4/1979 | Xanthopoulos | 604/192 |
| 4,260,077 | 4/1981 | Schroeder | 206/366 |
| 4,438,848 | 3/1984 | Mochow | 206/366 |
| 4,502,616 | 3/1985 | Meirerhoefer | 206/820 |
| 4,512,475 | 4/1985 | Federighi | 206/820 |

FOREIGN PATENT DOCUMENTS 0253426 5/1963 Australia .............................. 604/192

Primary Examiner—Stephen C. Pellegrino
Attorney, Agent, or Firm—John L. Voellmicke

[57] ABSTRACT

A syringe barrel assembly includes a plurality of syringe barrels each containing a barrel portion having an open proximal end, a chamber for retaining fluid, and a tip portion extending from a distal end of the barrel portion having a passageway therethrough. The passageway is adapted to accept the hub and second cannula of the hypodermic needle assembly having a hub, a first cannula extending outwardly from a distal end of the hub and a second cannula extending outwardly from a proximal end of the hub wherein the cannulae are in fluid communication. Piercable barrier means is provided in each of said passageways for preventing fluid communication between the chamber and the passageway. A plurality of web portions extending radially outwardly from the tip portions connects the syringe barrel. The web portions are integrally formed from the same material as the syringe barrels. The web portions and the syringe barrels are connected so that the syringe barrels are spaced apart from each other along the substantially straight line wherein the longitudinal axes of the syringe barrel are substantially parallel to each other.

18 Claims, 8 Drawing Sheets

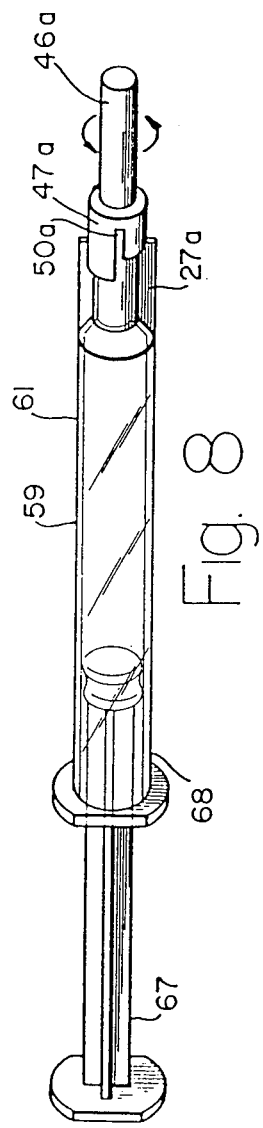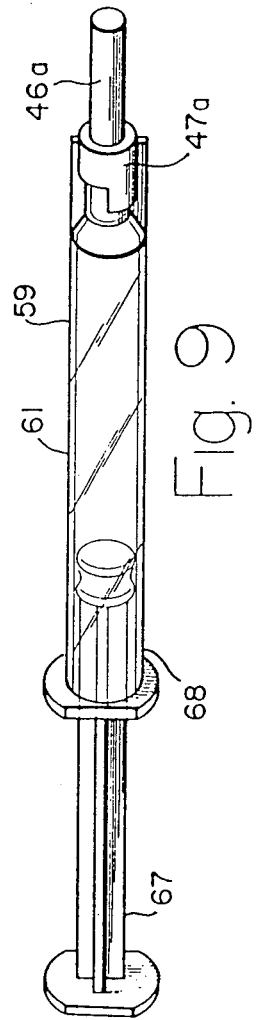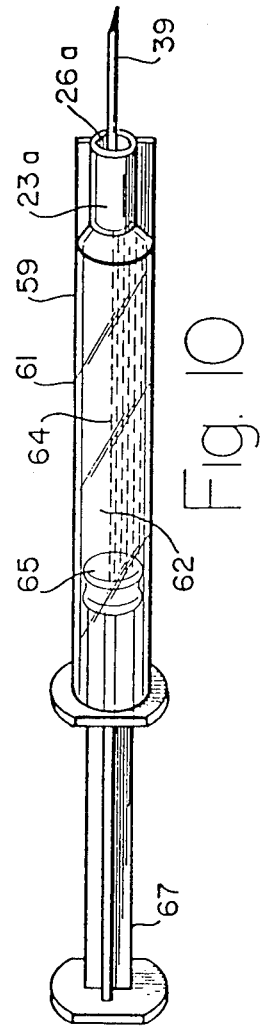

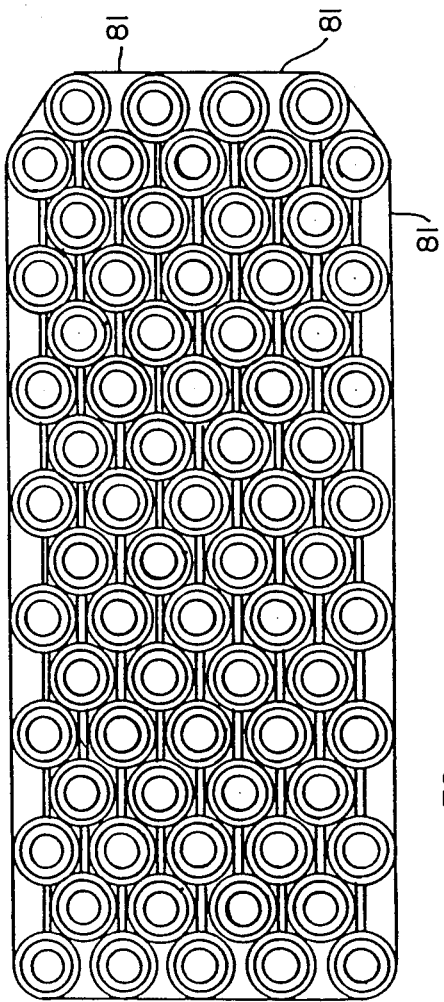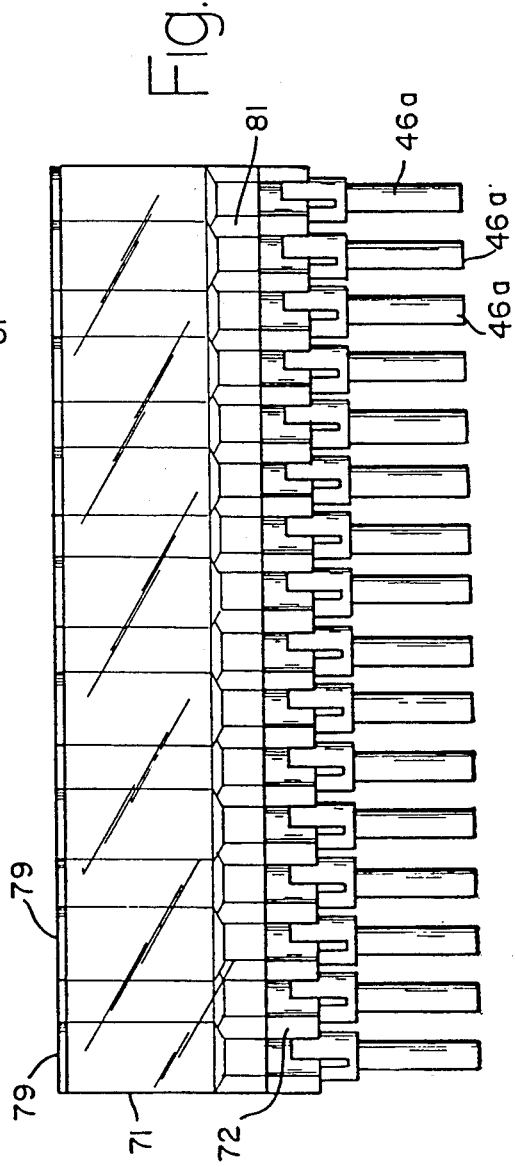

SYRINGE BARREL ASSEMBLY

BACKGROUND OF THE INVENTION

1. Field of the Invention

The present invention relates to a syringe barrel and hypodermic needle assembly, and an assembly of syringe barrels. More particularly, the present invention relates to a syringe barrel and hypodermic needle assembly wherein the hypodermic needle assembly contains a rearwardly facing cannula capable of piercing a barrier within the syringe barrel and to an assembly of a plurality of syringe barrels and integral web portions.

2. Description of the Prior Art

Generally speaking, a hypodermic syringe consists of a cylindrical barrel, most commonly made of plastic or glass, with a distal end adapted to be connected to a hypodermic needle and a proximal end adapted to receive a stopper and plunger rod assembly. One of the purposes of the stopper is to provide a relatively airtight seal between itself and the syringe barrel so that movement of the stopper up and down the barrel will cause liquid, blood or other fluids to be drawn into or forced out of the syringe through the distal end. The stopper is moved along the syringe barrel by applying axial force to a rigid plunger rod which is connected to the stopper and is sufficiently long to be accessible outside of the barrel. An example of a rigid barrel syringe is illustrated in U.S. Pat. No. 4,430,080 to Pasquini et al.

Also known to the art are hypodermic syringes having a flexible barrel portion, usually made of thermoplastic material, with a distal end adapted to be connected to a hypodermic needle. With a hypodermic needle attached, the user of a flexible barrel hypodermic syringe assembly may expel the medication by manually squeezing the flexible barrel portion forcing the medication through the hypodermic needle cannula and into the patient. A hypodermic syringe unit having a flexible barrel portion is illustrated in U.S. Pat. No. 2,680,440 to Fox.

A wide variety of injectable medications, or medications which can be rendered into injectable form by the addition of a diluent, are prefilled in rigid and flexible syringe barrel assemblies by pharmaceutical manufacturers, contract packagers, and the like. The medication containing syringes often sit many weeks or months before administration of medication to the patient. Under these circumstances, it is desirable to isolate the medication from the environment as thoroughly as possible. This task is more easily accomplished at the proximal end of the syringe where, in the case of a rigid syringe, a resilient rubber stopper can effectively seal the barrel. In the case of a flexible barrel syringe, the proximal end may be sealed shut, for example, by heat sealing, after the syringe is filled with medication. At the distal end of the syringe barrel the problem of isolating the medication from the environment is more difficult to solve. In rigid barrel syringes, it is common practice to seal the tip at the distal end of the syringe with elastomeric tip caps as described in U.S. Pat. No. 4,444,310 to Odell wherein the tip cap is removed at the time of use and a hypodermic needle assembly is placed over the syringe tip. In a rigid barrel syringe, the medication may also be isolated by placing an additional stopper in the syringe barrel so that the medication is contained between two resilient stoppers. When a stopper is used to provide needle isolation, additional structure in the syringe barrel is necessary to allow fluid to bypass the distal-most stopper. An example of this structure is illustrated in U.S. Pat. No. 3,330,282 to Visser et al.

In prefilled flexible barrel syringes, needle isolation may be accomplished by occluding the lumen of the cannula with a removable plug as illustrated in the above-mentioned patent to Fox. Also, needle isolation may be accomplished by providing a barrier between the medication and the syringe tip, and a hypodermic needle having a dual pointed cannula. At the time of use, the hypodermic needle may be moved in a rearward direction so that the rearmost cannula pierces the barrier establishing fluid communication between the chamber containing the medication and the hypodermic cannula. Such a syringe is illustrated in U.S. Pat. No. 4,018,222 to McAleer et al. A pierceable barrier design along the lines taught by McAleer et al. is advantageous with respect to its ability to isolate the medication from the environment, however, it has deficiencies in that the two-pointed cannula may be inadvertently activated by pressure on the needle shield which forces the cannula through the barrier.

Problems also exist in prefilling rigid or flexible syringe barrel. When filling, for example, thousands of syringe barrels, each of these syringe barrels must be delivered to a filling station, filled and then sealed. If the filling station contains multiple filling nozzles all of the syringe barrels in the area must be spaced appropriately so that each is in the proper position with respect to the filling nozzles, and then the syringe barrels are moved as a group to a sealing station which provides for sealing of the proximal ends of the barrels. A rigid barrel syringe may be sealed via introduction of a stopper into the barrel and a flexible barrel syringe may be sealed by compressing the proximal end of the barrel shut and applying heat energy to seal this end shut. One method of accomplishing multiple unit filling and sealing is to place the syringe barrels in a fixture which holds the syringe barrels at a predetermined distance from each other so that all the barrels in the fixture will be properly aligned with the filling station nozzles and, also, the subsequent sealing operation may be performed with the syringe barrels properly positioned. At the end of the operation the individual syringe barrels must be removed from the fixture so that the fixture may be returned and used again. This is a tedious operation requiring care to avoid contamination of the fixtures by spilled medication.

Rigid and flexible barrel syringe assemblies for use with prefilled medication, having structure for isolation of the medication from the environment, and methods of prefilling have been addressed by the prior art, as alluded to above. However, there is still a need for simple, straightforward, reliable, easily fabricated syringe assemblies for the storage and administration of medications. It is desirable that that syringe barrel effectively isolates the hypodermic needle cannula from the medication and the syringe assembly is easily activated, while being difficult to activate inadvertently. It is also desirable to have a group of syringes assembled in a configuration which will eliminate the use of separate fixtures during the prefilling operation.

SUMMARY OF THE INVENTION

An operable syringe barrel and hypodermic needle assembly of the present invention includes a barrel portion having a chamber for retaining fluid and a tip portion extending from a distal end of the barrel portion having a passageway therethrough. A projection extends outwardly from the tip portion. Piercable barrier means is provided for preventing fluid communication between the chamber and the passageway. A hub having a forward end, a rearward end and a conduit therethrough is movably positioned within the passageway. A first cannula extends outwardly from the forward end of the hub and a second cannula extends outwardly from the rearward end of the hub wherein the first cannula and the second cannula are in fluid communication with each other. A needle shield removably engages the tip, covering the first cannula. This needle shield includes an outer extension portion extending over a portion of the tip wherein the outer extension portion is capable of contacting the projection for limiting the motion of the needle shield toward the proximal end of the barrel. The outer extension portion includes a longitudinal groove which is wider than the projection and capable of receiving the projection. The needle shield also includes an inner extension portion projecting proximally into the passageway and capable of contacting the hub. The inner extension portion is long enough so that when the needle shield is rotated to align the groove and projection, and moved in a proximal direction with respect to the tip portion so that the projection enters the groove, the inner extension pushes against the hub and moves the hub in a proximal direction causing the second cannula to pierce the piercable barrier means.

In accordance with another embodiment of the present invention, an operable syringe barrel and hypodermic needle assembly includes an elongate barrel portion having an open proximal end and a chamber for retaining fluid. A tip portion extends from a distal end of the barrel portion and includes a passageway therethrough. A plainer web extends radially outwardly from the tip portion and is substantially parallel to the longitudinal axis of the tip portion. A piercable barrier extends across the passageway for preventing fluid communication between the chamber and the passageway. A rigid hub having a forward end, a rearward end and a conduit therethrough is movably positioned within the passageway. A first cannula extends outwardly from the forward end of the hub and a second cannula extends outwardly from the rearward end of the hub wherein the first cannula and the second cannula are in fluid communication with each other. An elongate hollow needle shield slidably engages the tip covering the first cannula. This needle shield has an outer skirt portion extending over a portion of the tip. The outer skirt portion is capable of contacting the web for limiting the motion of the needle shield toward the proximal end of the barrel. The outer skirt portion includes a longitudinal groove being wider than the web and capable of receiving the web. The needle shield includes an inner skirt portion projecting proximally into the passageway and capable of contacting the hub. The inner skirt portion is long enough so that when the needle shield is rotated to align the groove in the web, and moved in a proximal direction with respect to the tip portion so that the web enters the groove, the inner skirt pushes against the hub and moves the hub in a proximal direction causing the second cannula to pierce the piercable barrier.

Another aspect of the present invention is a syringe barrel assembly comprising a plurality of syringe barrels each including a barrel portion having a open proximal end, a chamber for retaining fluid, and a tip portion extending from a distal end of the barrel portion having a passageway therethrough. The passageway is adapted to accept the hub and second cannula of a hypodermic needle assembly having a hub, a first cannula extending outwardly from a distal end of the hub and a second cannula extending outwardly from a proximal end of the hub wherein the cannulae are in fluid communication. Piercable barrier means is included in each of the passageways for preventing fluid communication between the chamber and the passageway of each syringe barrel. A plurality of web portions extend radially outwardly from the tip portions connecting the syringe barrels. The web portions are integrally formed from the same material as a syringe barrel. The web portions in the syringe barrels are connected so that the syringe barrels are spaced apart from each other along a substantially straight line wherein the longitudinal axes of the syringe barrels are substantially parallel to each other.

Another embodiment of this other aspect of the present invention is a syringe barrel assembly comprising a plurality of thermoplastic syringe barrels each including a barrel portion having an open flexible proximal end, a flexible chamber for retaining fluid, and a tip portion extending from a distal end of the barrel having a passageway therethrough. The passageway is adapted to accept the hub and second cannula of a hypodermic needle assembly having a hub, a first cannula extending outwardly from a distal end of the hub and a second cannula extending outwardly from a proximal end of the hub wherein the cannulae are in fluid communication. Piercable barrier means is included in each of the passageways for preventing fluid communication between the chamber and the passageway. A plurality of plainer web shaped portions extending radially outwardly from the tip portions connects the syringe barrels. The web portions are substantially parallel to the longitudinal axis of the tip portions. The web portions are integrally formed from the same thermo-plastic material as the syringe barrels. The web portions and the syringe barrels are connected so that the syringe barrels are spaced apart from each other along a substantially straight line.

In accordance with the principles of the present invention, a number of advantages and objectives are attained. The present invention provides a simple straightforward, reliable, easily fabricated syringe barrel and hypodermic needle assembly for the storage and administration of medication, wherein the structure of the syringe barrel and hypodermic needle assembly effectively isolates the hypodermic needle cannula from the medication before the time of use while the syringe barrel and hypodermic needle assembly is easily activated intentionally while being difficult to activate inadvertently. Another aspect of the instant invention provides a syringe barrel assembly which holds and orients the syringe barrels with respect to each other in order to minimize the need for additional fixturing during prefilling and sealing operations.

BRIEF DESCRIPTION OF THE DRAWINGS

FIG. 8 is a perspective view of another embodiment of the present syringe barrel and hypodermic needle assembly wherein the barrel portion is rigid;

FIG. 9 is a perspective view of the syringe barrel and hypodermic needle assembly of FIG. 8 illustrating the position of the needle shield when the needle assembly is in fluid communication with the chamber;

FIG. 10 is a perspective view of the syringe barrel and hypodermic needle assembly of FIG. 9 with the needle shield removed;

FIG. 13 is a side elevation view of a plurality of syringe barrel assemblies nested together in rows;

FIG. 14 is a top plan view of the plurality of syringe barrel assemblies of FIG. 13.

DETAILED DESCRIPTION

Figure 1:
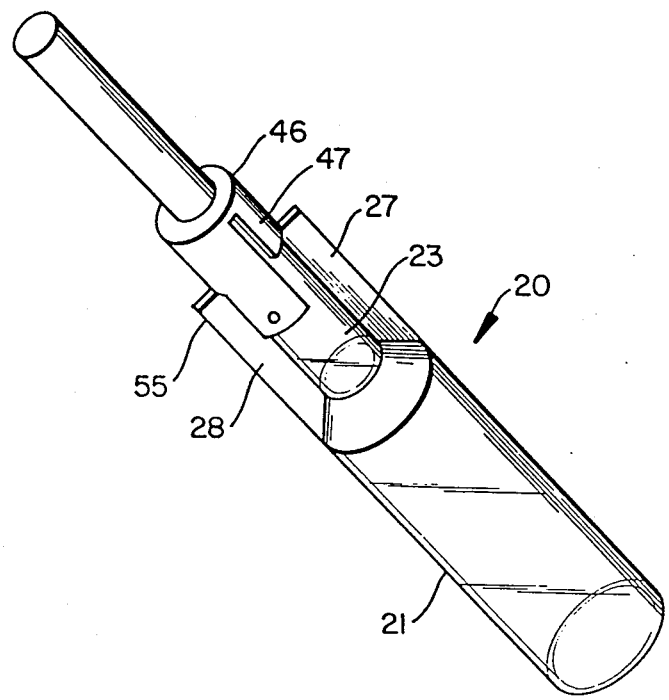
FIG. 1 is a perspective view of the syringe barrel and hypodermic needle assembly of the present invention.
Figure 2:
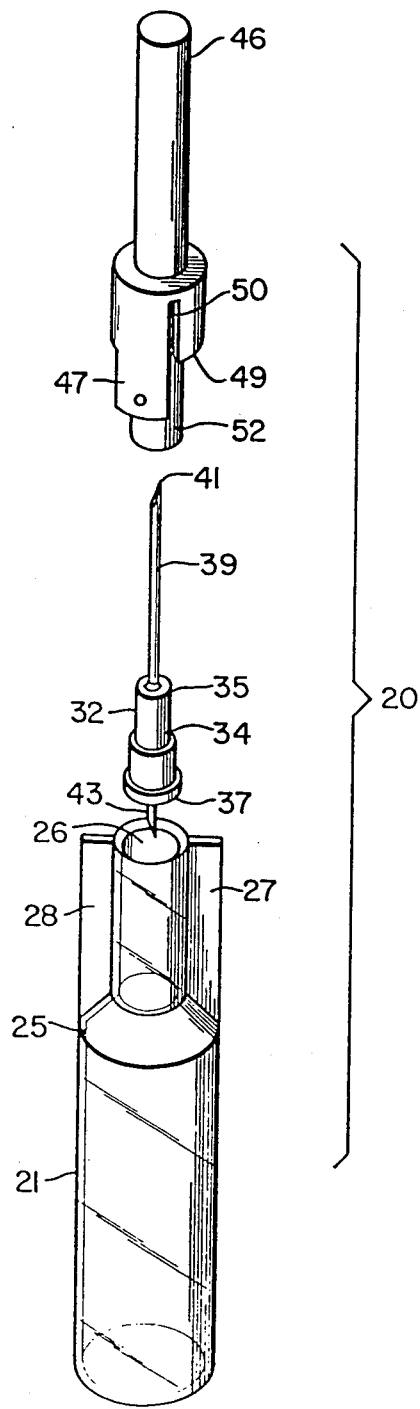
FIG. 2 is an exploded perspective view of the components of the syringe barrel and hypodermic needle assembly of FIG. 1.
Figure 3:
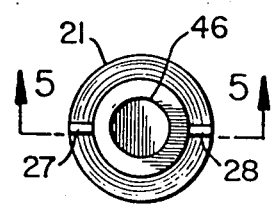
FIG. 3 is a top plan view of the syringe barrel and hypodermic needle assembly of FIG. 1.
Figure 4:
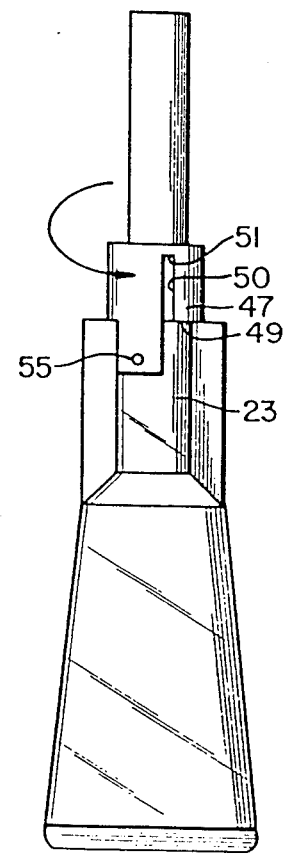
FIG. 4 is a side elevation view of the syringe barrel and hypodermic needle assembly of FIG. 1 shown with the proximal end of the barrel portion sealed.

While the invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1-7, an operable syringe barrel and hypodermic needle assembly 20 includes an elongate barrel portion 21 having a chamber 22 for retaining fluid. A tip portion 23 extends from distal end 25 of the barrel portion and includes passageway 26. For purposes of the description of the present invention, the term "distal end" is intended to refer to the end furthest from the person holding the syringe, whereas the term "proximal end" is meant to refer to the end closest to the holder of the syringe.

A planar web 27 extends radially outwardly from the tip portion. A second planar web 28 extends radially outwardly from the tip portion and is oppositely disposed from planar web 27. These webs are substantially parallel to longitudinal axis 29 of the tip portion. A pierceable barrier 31 extends across passageway 26 for preventing fluid communication between chamber 22 and the passageway. In this preferred embodiment, the pierceable barrier is integrally formed partition of the same material as the tip portion and barrel portion. However, it is within the purview of the instant invention to include a pierceable barrier structure made of different material which is attached to the barrel portion and/or the tip portion via adhesive bonding, ultrasonic welding or other suitable means and that the integral barrier illustrated is exemplary of these many possibilities.

Figure 5:
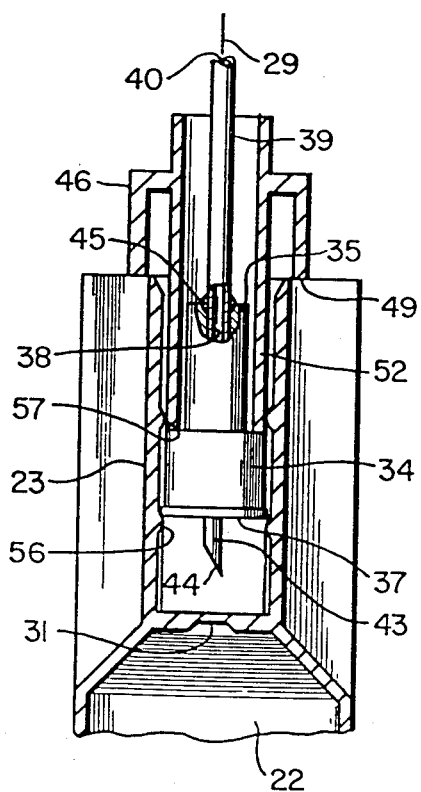
FIG. 5 is a partial enlarged cross-sectional view of the syringe barrel and hypodermic needle assembly of FIG. 3 taken along lines 5—5.

A needle assembly 32 includes a rigid hub 34 having a forward end 35 and a rearward end 37 and a hub passageway or conduit 38 therethrough. Hub 34 is movably positioned within passageway 26. A first cannula 39, having a lumen 40 therethrough, extends outwardly from the forward end of the hub terminating in a sharpened tip 41 adapted to penetrate human flesh. A second cannula 43 having a lumen (not shown) therethrough extends outwardly from rearward end 37 of the hub and terminates in a sharpened tip 44 adapted to penetrate pierceable barrier 31 to establish fluid communication between chamber 22 and the second cannula. In the preferred embodiment as best illustrated in FIG. 5, the first cannula and the second cannula are made of one piece construction and held in position with respect to the hub via adhesive 45, such as epoxy, UV curable adhesive, heat curable adhesive and the like. It is within the purview of the present invention to include separate cannula wherein the lumens of the separate cannula are joined by the hub passageway or conduit in the hub to form a continuous fluid path from the tip of the second cannula to the tip of the first cannula. It is also within the purview of the instant invention to include a hub wherein the second cannula is integrally molded from the hub material and not a separate component. The one-piece cannula structure of the preferred embodiment is exemplary of these many structural possibilities wherein the first cannula and the second cannula are in fluid communication.

An elongate hollow needle shield 46 slidably engages tip portion 23 while covering first cannula 39. The needle shield includes an outer extension or outer skirt portion 47 extending over a portion of the tip. The outer extension or outer skirt portion includes intermediate surface 49 which contacts web 27 for limiting the motion of the needle shield toward the proximal end of the barrel. Outer extension or outer skirt portion 47 also includes longitudinal groove 50 which is wider than web 27 and capable of receiving web 27 when the needle shield is rotated so that web 27 and groove 50 are aligned. When web 27 and groove 50 are aligned, the needle shield is capable of moving toward the proximal end of the syringe barrel without being obstructed by the structure of the outer skirt portion, so long as web 27 does not contact base 51 of the groove.

Figure 6:
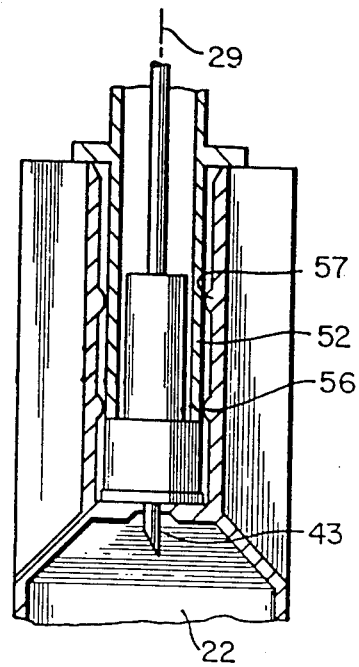
FIG. 6 is an enlarged partial cross-sectional view, similar to the cross-sectional view of FIG. 5, showing the second cannula piercing the barrier to establish fluid communication between the hypodermic needle assembly and the chamber.

Needle shield 46 also includes an inner projection or inner skirt 52 projecting downwardly in a proximal direction into passageway 26 and capable of contacting hub 34, preferably at forward end 35 of the hub. Inner skirt portion 52 is long enough so that when the needle shield is rotated to align groove 50 with web 27 and the needle shield is moved in a proximal direction with respect to the tip portion, web 27 enters groove 50 while inner skirt 52 pushes against the hub and moves the hub in a proximal direction causing second cannula to pierce the pierceable barrier, establishing fluid communication between the chamber and the second cannula, as best illustrated in FIG. 6. The structure of the instant invention which requires the deliberate act of rotating the needle shield to align groove 50 and web 27 helps overcome a major deficiency of the prior art which is inadvertent activation of the syringe by applying force to the needle shield. With the instant invention inadvertent force applied to the needle shield along its longitudinal axis will not cause second cannula to pierce the barrier unless the needle shield is deliberately oriented to align the groove and the web.

It should be noted that inner skirt portion 52 is preferably, but not necessarily, circularly shaped having a substantially circularly shaped cross section. The inner skirt portion is a projection and may assume a variety of shapes, such as rod-shaped, so long as the projection has the structural integrity necessary to move the needle assembly, and force the second cannula through the pierceable barrier. Further, the shape of outer skirt portion is preferably, but not necessarily, circularly shaped having a substantially circularly shaped cross section. The circular shape of the outer skirt portion is desirable because it provides a rounded knob-like surface for the user to hold the needle shield for the purpose of rotating it or moving it in a longitudinal direction.

It should also be noted that the planar shape of web 27 is the preferred shape of the structure which interacts with groove 50 in the needle shield. However, other projection structures such as a pin or a cantilever member projecting radially outwardly from the tip are also suitable, and within the purview of the present invention. It is also within the purview of the instant invention to include a barrel portion with more than one projection or planar web, and a needle shield with one or more grooves and that the number of grooves does not necessarily have to equal the number of webs so long as one web portion engages one groove to allow movement of the needle shield in a distal direction. It may be desirable to extend the outer skirt portion for more than 180 degrees and to include two web portions on the syringe barrel and two grooves in the outer skirt portion of the needle shield.

This preferred embodiment also includes retention means for holding the needle shield in the predetermined angular position with respect to the tip portion, before use. The retention means preferably includes a weld portion 55 wherein a small portion of the outer skirt is attached to the outer surface of the tip through the application of heat energy, ultrasonic energy, adhesive or other suitable means. The weld portion holds the needle shield in a position which can be changed only by applying a rotational force to the needle shield, with respect to the barrel, which will shear the weld portion at the interface between the needle shield and the syringe barrel. The weld portion provides additional help to overcome a deficiency of the prior art in that it helps prevent the inadvertent activation of the syringe by increasing the force required to align the web portion on the tip and the groove in the needle shield. This weld portion also provides tamper evidence, warning the user of potential contamination of syringe barrel assemblies wherein the weld is broken. An alternative positioning means can include a suitable film or paper (not shown) adhesively attached to the outer skirt portion and the syringe barrel or tip so that forced rotation of the needle shield will cause the paper to shear and rip along the interface between the needle shield and the syringe barrel or tip, again helping to prevent inadvertent activation and providing tamper evidence for the user.

Tip portion 23 also includes a first protuberance 56 projecting radially inwardly into passageway 26. Protuberance 56 is shaped to allow the hub to pass thereover when manual force is applied to the hub through the needle shield. A second protuberance 57 is positioned distally with respect to the first protuberance and projects radially inwardly into the passageway. This second protuberance is shaped to prevent the hub from coming out of the passageway when the needle shield is removed and the syringe is used for mixing the medication and/or for injecting medication. As best illustrated in FIG. 5, a portion of the hub of needle assembly 32 can be placed between protuberances 56 and 57 to hold the hub in a predetermined, desirable, position along the passageway, before use, wherein the second cannula preferably does not contact the pierceable barrier. During use, the hub may be forced over the first protuberance so that the second cannula may pierce the pierceable barrier. Also, in this preferred embodiment the outside diameter of the inner skirt portion is slightly larger than the inside diameter of the passageway at the position of the second protuberance so that there is a frictional interference fit which helps prevent the unintentional removal of the needle shield by requiring an applied force to move the needle shield with respect to the tip portion.

Figure 7:
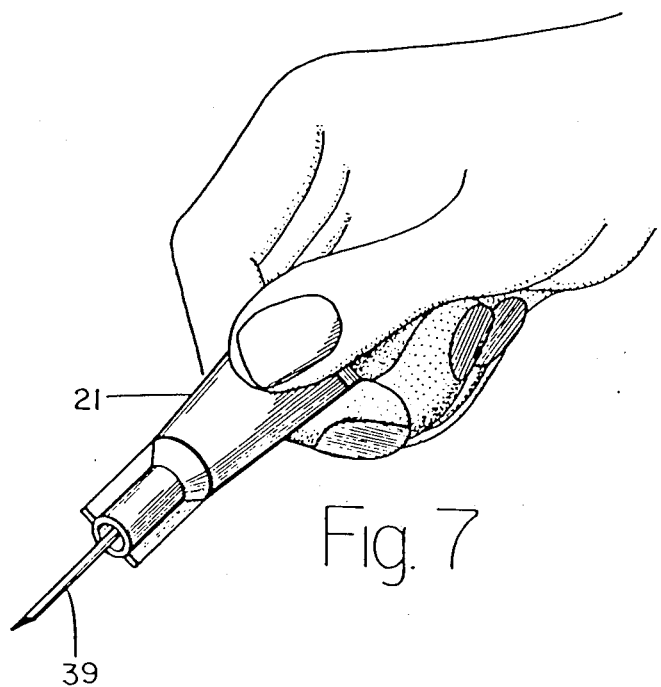
FIG. 7 is a perspective view illustrating the expulsion of medication from the syringe barrel using digital force.
Figure 11:
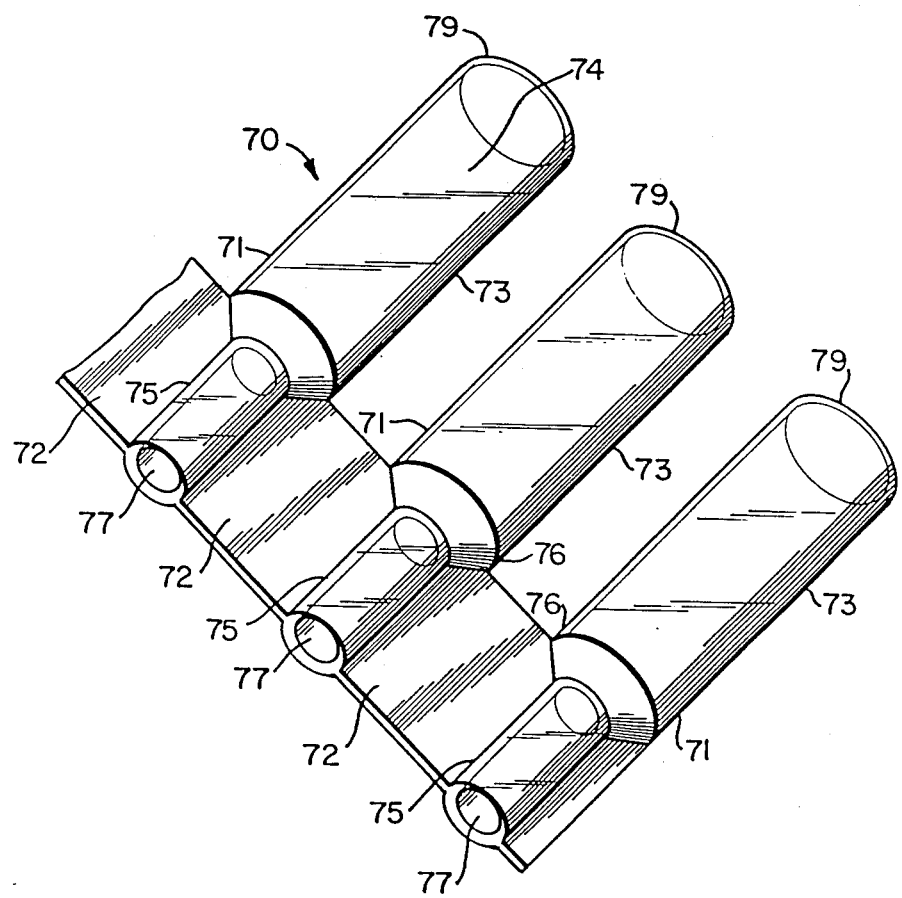
FIG. 11 is a perspective view of the syringe barrel assembly of the present invention.
Figure 12:
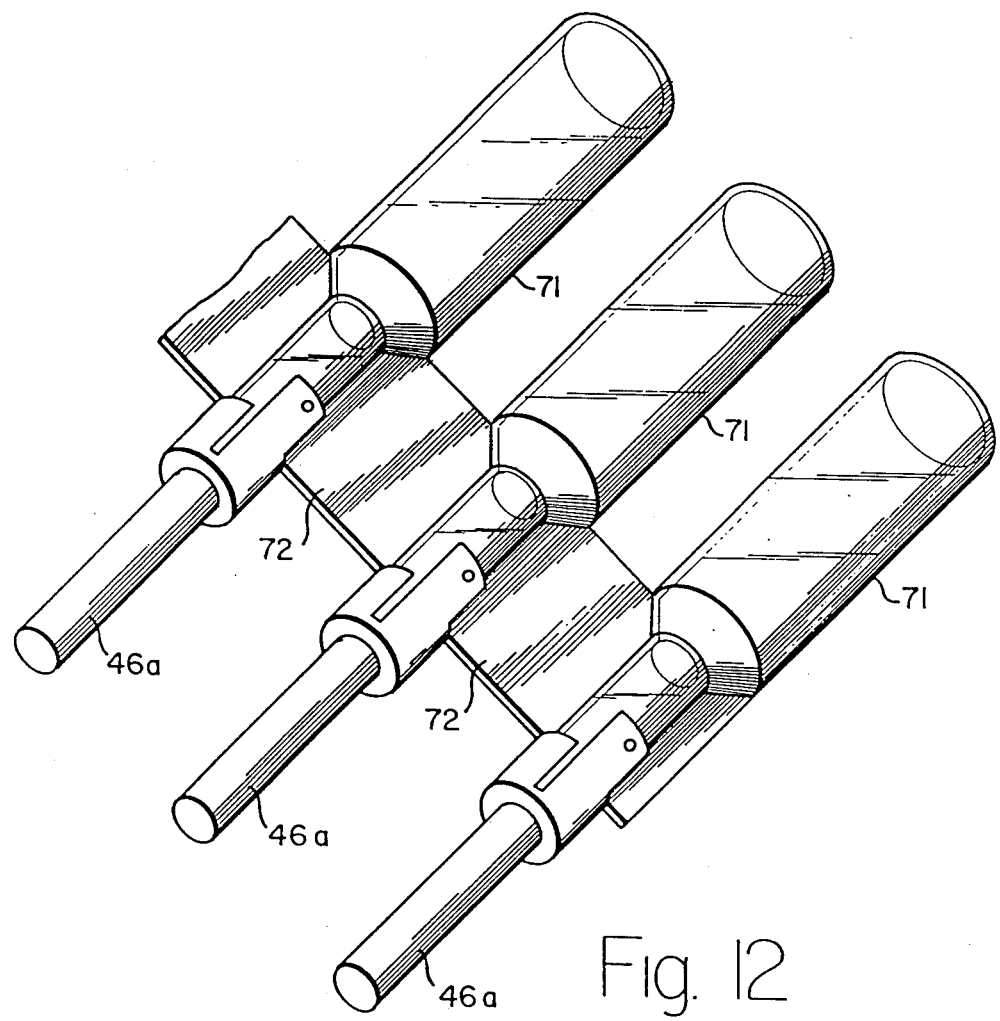
FIG. 12 is a perspective view of the syringe barrel assembly of the present invention with needle shields attached.

The steps required for placing medication in elongate barrel 21 and sealing its flexible proximal end will be discussed in more detail hereinafter. After the barrel is filled with medication and sealed, the medication is isolated from the environment until the user causes the second cannula to pierce the pierceable barrier and establishes fluid communication between the chamber and the needle assembly. At this point, the syringe barrel and hypodermic needle assembly is ready to use for administering an injection wherein the medication may be forced out of the syringe barrel using digital pressure as illustrated in FIG. 7. If the syringe contains a dry medication in powder or lyphilized form, the diluent usually contained in a vial with a piercable stopper, will have to be mixed with the powdered medication before administration of the injection. To do this, the syringe and barrel assembly is activated, the first cannula is inserted into a source of diluent and the barrel is digitally depressed to substantially remove the air contained therein, where upon the removal of the digital pressure will draw the diluent into the syringe barrel for mixing. At this point, the first cannula is removed from the vial and the injection may be administered.

FIGS. 8-10 illustrate an alternative embodiment of the syringe barrel and hypodermic needle assembly of the present invention further including a plunger rod and stopper assembly. In this alternative embodiment the structure at the distal end of the barrel including the needle shield, the needle assembly and the tip portion of the barrel are substantially identical to the embodiments of FIGS. 1-7. Accordingly, substantially similar components performing substantially similar functions will be numbered identically to those components in the embodiment of FIGS. 1-7, except that a suffix "a" will be used to identify these components in FIGS. 8-10. An operable syringe barrel and hypodermic needle assembly 59 includes a barrel portion 61 having a chamber 62 for retaining fluid and a tip portion 23a having a passageway 26a therethrough. A planar web 27a extends radially outwardly from said tip portion wherein the web is substantially parallel to the longitudinal axis of the tip portion. A pierceable barrier (not shown) extends across the passageway for preventing fluid communication between the chamber and the passageway. A rigid hub (not shown) is slidably positioned within passageway 26a. A first cannula 39a extends outwardly from the forward end of the hub and a second cannula (not shown) extends outwardly from the rearward end of the hub wherein the first and the second cannula are in fluid communication.

A needle shield 46a slidably engages tip portion 23a. Needle shield 46a includes outer skirt portion 47a extending over a portion of the tip. The outer skirt portion is capable of contacting planar web portion 27a for limiting the motion of the needle shield toward the proximal end of the barrel. The outer skirt portion also includes longitudinal groove 50a which is wider than web 27a and capable of receiving web 27a. The needle shield also includes an inner skirt portion (not shown) projecting proximally into the passageway and capable of contacting the hub. This inner skirt portion is long enough so that when the needle shield is rotated to align groove 50a with web 27a, and moved in a proximal direction with respect to the tip portion so that the web enters the groove, the inner skirt will push against the hub and move the hub in a proximal direction causing the second cannula (not shown) to pierce the pierceable barrier (not shown) establishing fluid communication between the interior of the syringe barrel and the second cannula.

In this alternative embodiment the portion of elongate barrel portion 61 defining the chamber is rigid and has the substantially circularly shaped cross section. In addition to the syringe barrel and hypodermic needle assembly, a quantity of liquid medication 64 is placed in chamber 62. A stopper 65 is slidably positioned in fluid-tight engagement inside barrel portion 61. A rigid plunger rod 67 engages stopper 65 and extends outwardly from proximal end 68 of the barrel portion. The plunger rod is accessible outside the barrel portion so that force can be applied to the plunger rod to move the stopper within the barrel to force medication through the needle assembly during the injection process.

Referring now to FIGS. 11–14, another aspect of the present invention includes a syringe barrel assembly 70 having a plurality of syringe barrels 71 each including a barrel portion 73 having a chamber 74 for retaining fluid. A tip portion 75 extends from distal end 76 of the barrel portion having a passageway 77 therethrough. The passageway is adapted to accept the hub and second cannula of a hypodermic needle assembly having a hub, a first cannula extending outwardly from a distan end of said hub and a second cannula extending outwardly from a proximal end of said feel whereas said cannulae are in fluid communication. A pierceable barrier (not shown) is positioned in passageway 77 for preventing fluid communication between chamber 74 and the passageway. A plurality of planar shaped web portions 72 extend radially outwardly from the tip portions connecting the syringe barrels. It is preferred that the web portions are substantially parallel to the longitudinal axis of the tip portions. The web portions are integrally formed of the same material as the syringe barrels. The web portions and the syringe barrels are connected so that the barrels are spaced apart along a substantially straight line wherein the longitudinal axes of said syringe barrels are substantially parallel to each other. It is preferred, but not necessary, that the barrels be equally spaced from each other along the web portions.

The syringe barrel assembly contains syringe barrels which are ready for sterilization, filling and sealing. The filling operation, which will be explained in more detail hereinafter, can be performed by delivering medication through open proximal end 79 of the syringe barrel and then sealing the barrel shut by compressing the open proximal end and applying heat energy or heat producing energy or by other suitable means. Tip portion 75 of the syringe barrels is substantially identical to the tip portion in the embodiment of FIGS. 1–7. The syringe barrels are illustrated with needle shield 46a which is substantially identical to needle shield 46 in the embodiments of FIGS. 1–7 to show that a needle assembly and needle shield may be attached to the syringe barrels before filling or after filling. In filling syringe barrels, in general, it is common practice to place a number of syringe barrels in a fixture which aligns the syringe barrels and spaces them apart in a predetermined manner so that the group of syringes may be filled in a multiple head filling device wherein a plurality of nozzles deliver liquid or solid medication into a plurality of open-ended syringe barrels aligned therewith. Also, the syringe barrels, when in the fixture, may be indexed through a filling station, one at a time or a row at a time, until all barrels are filled. In some cases, the next step may be subjecting the filled syringe barrels to a lyophilization procedure to remove water from the medication. The last step is to individually, or in a group, seal the proximal end of the syringe barrel from the environment.

The instant invention offers the advantage of providing a plurality of syringe barrels and integral web portions holding the syringe barrels in a relative position with respect to each other so that it may not be necessary to use specific fixtures or dies to carry the syringe barrels through a filling and sealing process because the web portions act as a fixture holding the syringe barrels in a predetermined spaced relationship. In an automated filling and sealing operation, the syringe barrels can be indexed through the filling and sealing stations relying on the web material to hold the relative position of the syringe barrels. Also, the present invention allows the grouping of a plurality of syringe barrels as best illustrated in FIGS. 13 and 14. Here the assemblies are nested together in rows so that the individual barrels in alternate rows are in approximate alignment with each other forming orthogonal rows and columns of syringe barrels in the alternate rows. It is preferred that the groups of nested syringe barrel assemblies be mechanically held together in their relative positions so that they may be, preferably, filled and sealed in a group. One possible method of holding the plurality of syringe barrel assemblies together is the use of known plastic shrink wrap material 81. This material will hold the syringe barrel assemblies together through the filling and sealing operation and can be cut or torn away after the syringes are filled with medication.

The instant invention offers the further advantage that a syringe barrel manufacturer can produce large quantities of syringe barrel assemblies in accordance with the present invention, shrink wrap groups of syringe barrel assemblies together, place the assemblies in a bacteria impervious package which will exclude bacteria from the contents, and sterilize said package and its contents. This sterile package of nested syringe barrel assemblies may then be sold to pharmaceutical manufacturers or hospitals for filling with medication and sealing. It will be apparent to one skilled in the art that there are many possibilities for placing syringe barrels along webs in equal or unequal spacing positions and for joining adjacent rows of syringe barrel assemblies so that they nest or rest in some other tangential relationship with each other and that the equally spaced syringe barrels nested as illustrated in FIG. 14, is exemplary of these many possibilities. It is also within the purview of the present invention to include substantially long web syringe barrel assembly, containing perhaps several hundred syringe barrels, wherein the web and syringe barrel assemblies are rolled in coils for feeding into filling and sealing devices along a straight line.

Figure 15:
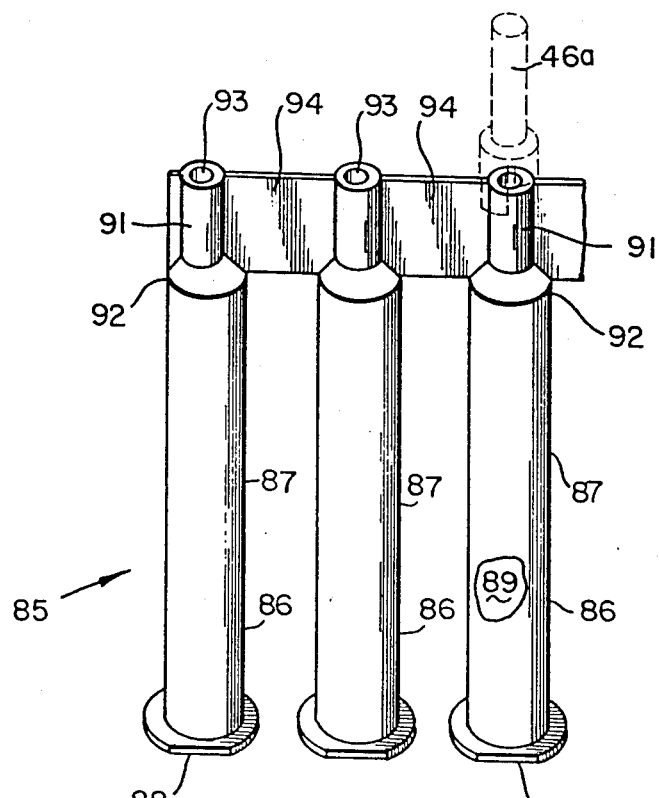
FIG. 15 is a perspective view of another embodiment of the syringe barrel assembly of the present invention wherein the barrel portions are rigid.

Adverting to FIG. 15, in another embodiment of the present invention, a syringe barrel assembly 85 includes a plurality of thermoplastic syringe barrels 86 each including a rigid cylindrical barrel portion 87 having an open proximal end 88 and a chamber 89 for retaining fluid. A tip portion 91 extends from distal end 92 of the barrel portion and includes a passageway 93 therethrough. Piercable barrier means is provided for sealing each of the passageways so that fluid cannot leave the chamber therethrough. In this embodiment a pierceable barrier (not shown) is positioned in each of the passageways. The barrier may be pierced by a dual pointed needle assembly as taught hereinabove. A plurality of web portions 94 between the syringe barrels connects the syringe barrels. The web portions are integrally formed from the same thermoplastic material as the syringe barrels. The web portions and the syringe barrels are connected so that the syringe barrels are spaced apart from each other along a substantially straight line wherein the longitudinal axis of the syringe barrels are substantially parallel to each other. The syringe barrel assembly of the present embodiment may be used in conjunction with the dual cannula needle assembly and needle shield of FIGS. 1-7 wherein this needle shield is shown in phantom lines and indicated as 46a in FIG. 15.

After filling the syringe barrels with medication and sealing the proximal end of the barrels, the barrels may be separated by shearing the web portion between adjacent barrels. The web portion may be sheared so that substantially most of it is discarded or partially removed, such as in the embodiments of FIGS. 1-7 wherein the remaining portion of the web acts as a structure which interacts with the needle shield to help precent inadvertent piercing of the barrier. The web may be sheared in a press using spaced dies, or with a hot wire or other suitable means.

The syringe barrels of the present invention may be constructed of thermoplastic material such as polypropylene and polyethylene. For embodiments where the barrel portion and the proximal end of the barrel are flexible it will be necessary to form the syringe barrel of substantially thinner sections of material to provide the flexibility necessary. A wide variety of materials are suitable for the stopper with natural rubber and butyl rubber being preferred. A wide variety of rigid materials are suitable for the plunger rod with thermoplastic materials such as polypropylene, polyethylene and polystyrene being preferred. A wide variety of rigid materials are suitable for constructing the hub, for use in the needle assembly, with thermoplastic materials such as polypropylene and polyethylene being preferred. It is preferred that the first cannula and the second cannula be formed of medical grade stainless steel. However, it is possible to form the hub and the second cannula out of one-piece thermoplastic material such as ABS, polypropylene or polyethylene. It may also be desirable to apply a medical grade lubricant, such as medical grade silicone lubricant, to the outside of the first cannula to reduce the force required for the cannula to penetrate the patient's flesh. It is preferred that all elements of the syringe barrel and hypodermic needle assembly, and the syringe barrel assembly of the instant invention be sterile when used. Accordingly, materials should be selected for compatibility with the sterilization process being used.

Thus, it can be seen that the present invention provides a simple, straightforward, reliable, easily fabricated syringe barrel and hypodermic needle assembly for the storage and administration of medication, wherein the structure of the syringe barrel and hypodermic needle assembly effectively isolates the hypodermic needle cannula from the medication before the time of use and the syringe is easily activated intentionally while being difficult to activate inadvertently. Another aspect of the instant invention provides a syringe barrel assembly which holds and orients the syringe barrels with respect to each other in order to eliminate the need for additional fixturing during prefilling and sealing operations.

What is claimed is:

1. A syringe barrel assembly comprising:
a plurality of syringe barrels each including a barrel portion having an open proximal end, a chamber for retaining fluid, and a tip portion extending from a distal end of said barrel portion having a passageway therethrough;
pierceable barrier means in each of said passageways for preventing fluid communication between said chamber at said passageway; and
a plurality of web portions extending radially outwardly from said tip portions connecting said syringe barrels, said web portions being integrally formed from the same material as said syringe barrels, said web portions and said syringe barrels being connected so that said syringe barrels are spaced apart from each other along a substantially straight line wherein the longitudinal axes of said syringe barrels are substantially parallel to each other;
a hub movably positioned in each of said passageways, said hub having a forward end, a rearward end and a conduit therethrough;
a first cannula extending outwardly from said forward end of each of said hubs and a second cannula extending outwardly from said rearward end of each of said hubs, said first cannula and said second cannula being in fluid communication;
a needle shield movably engaging each of said tips covering said first cannula, said needle shield having an outer extension portion extending over a portion of said tip, said outer extension portion being capable of contacting said web portion for limiting the motion of said needle shield toward the proximal end of said barrel, said outer extension portion including a longitudinal groove being wider than said web portion and capable of receiving said web portion; and
said needle shield having an inner extension portion projecting proximally into said passageway and capable of contacting said hub, said inner extension portion being long enough so that when said needle shield is rotated to align said groove and said web portion, and moved in a proximal direction with respect to said tip portion so that said web portion enters said groove, said inner extension portion pushes against said hub and moves said hub in a proximal direction causing said second cannula to pierce said pierceable barrier means.

2. The syringe barrel assembly of claim 1 wherein said syringe barrels are spaced equally from each other when the distance between said syringe barrels is measured along said web portions.

3. The syringe barrel assembly of claim 1 wherein each of said web portions is planar shaped.

4. The syringe barrel assembly of claim 3 wherein said web portions are parallel to the longitudinal in its place of said tip portions.

5. The syringe barrel assembly of claim 1 wherein the portion of said barrel portions defining said chambers and said proximal end of each of said barrel portions are flexible.

6. The syringe barrel assembly of claim 5 wherein said flexible portions of said barrel portions are capable of being deformed by application of digital pressure.

7. The syringe barrel assembly of claim 6 further including a quantity of medication in each of said chambers.

8. The syringe barrel assembly of claim 7 wherein said proximal end of each of said barrel portions is sealed shut forming a fluid-tight chamber.

9. The syringe barrel assembly of claim 1 wherein the portion of said barrel portion defining said chamber of each of said syringe barrels is rigid and has a substantially circularly shaped cross section.

10. The syringe barrel assembly of claim 9 further including a quantity of medication in each of said chambers.

11. The syringe barrel assembly of claim 10 further including a stopper slidably positioned in fluid-tight engagement inside each of said barrel portions adapted to engage a plunger rod to facilitate its operation.

12. The syringe barrel assembly of claim 1 wherein said syringe barrel assembly is made of thermoplastic material.

13. The syringe barrel assembly of claim 12 wherein said thermoplastic material is selected from the group consisting of polypropylene and polyethylene.

14. A plurality of syringe barrel assemblies in accordance with claim 1 wherein said syringe barrel assemblies are nested together in rows so that the individual syringe barrels in alternate rows are in approximate alignment with each other forming orthogonal rows and columns of said syringe barrels in said alternate rows.

15. The plurality of syringe barrel assemblies of claim 14 further including holding means for holding said syringe barrel assemblies together in said nesting relationship during handling.

16. The plurality of syringe barrel assemblies of claim 15 further including a bacteria impervious package enveloping said syringe barrel assemblies.

17. A syringe barrel assembly comprising:
a plurality of thermoplastic syringe barrels each including a barrel portion having an open flexible proximal end, a flexible chamber for retaining fluid, and a tip portion extending from a distal end of said barrel portion having a passageway therethrough;
pierceable barrier means in each of said passageways for preventing fluid communication between said chamber and said passageway; and
a plurality of planar shaped web portions extending radially outwardly from said tip portions connecting said syringe barrels, said web portions being substantially parallel to the longitudinal axis of said tip portions, said web portions being integrally formed from the same thermoplastic material as said syringe barrels, said web portions and said syringe barrels being connected so that said syringe barrels are spaced apart from each other along a substantially straight line;
a hub movably positioned in each of said passageways, said hub having a forward end, a rearward end and a conduit therethrough;
a first cannula extending outwardly from said forward end of each of said hubs and a second cannula extending outwardly from said rearward end of each of said hubs, said first cannula and said second cannula being in fluid communication;
a needle shield movably engaging each of said tips covering said first cannula, said needle shield having an outer extension portion extending over a portion of said tip, said outer extension portion being capable of contacting said web portion for limiting the motion of said needle shield toward the proximal end of said barrel, said outer extension portion including a longitudinal groove being wider than said web portion and capable of receiving said web portion; and
said needle shield having an inner extension portion projecting proximally into said passageway and capable of contacting said hub, said inner extension portion being long enough so that when said needle shield is rotated to align said groove and said web portion, and moved in a proximal direction with respect to said tip portion so that said web portion enters said groove, said inner extension portion pushes against said hub and moves said hub in a proximal direction causing said second cannula to pierce said pierceable barrier means.

18. A syringe barrel assembly comprising:
a plurality of thermoplastic syringe barrels each including a rigid cylindrical barrel portion having an open proximal end, a chamber for retaining fluid, and a tip portion extending from a distal end of said barrel portion having a passageway therethrough;
pierceable barrier means in each of said passageways for preventing fluid communication between said chamber and said passageway; and
a plurality of web portions between said syringe barrels and connecting said syringe barrels, said web portions being integrally formed from the same thermoplastic material as said syringe barrels, said web portions and said syringe barrels being connected so that said syringe barrels are spaced apart from each other along a substantially straight line wherein the longitudinal axes of said syringe barrels are substantially parallel to each other;
a hub movably positioned in each of said passageways, said hub having a forward end, a rearward end and a conduit therethrough;
a first cannula extending outwardly from said forward end of each of said hubs and a second cannula extending outwardly from said rearward end of each of said hubs, said first cannula and said second cannula being in fluid communication;
a needle shield movably engaging each of said tips covering said first cannula, said needle shield having an outer extension portion extending over a portion of said tip, said outer extension portion being capable of contacting said web portion for limiting the motion of said needle shield toward the proximal end of said barrel, said outer extension portion including a longitudinal groove being wider than said web portion and capable of receiving said web portion; and said needle shield having an inner extension portion projecting proximally into said passageway and capable of contacting said hub, said innner extension portion being long enough so that when said needle shield is rotated to align said groove and said web portion, and moved in a proximal direction with respect to said tip portion so that said web portion enters said groove, said inner extension portion pushes against said hub and moves said hub in a proximal direction causing said second cannula to pierce said pierceable barrier means.

* * * * *